US008920855B1

(12) United States Patent
Irmiter

(10) Patent No.: US 8,920,855 B1
(45) Date of Patent: Dec. 30, 2014

(54) METHODS OF TOPICALLY TREATING TINNITUS AND RELATED DISORDERS

(71) Applicant: Charles Irmiter, Richfield, MN (US)

(72) Inventor: Charles Irmiter, Richfield, MN (US)

(73) Assignee: Setem Hemth, Inc, Los Angeles, CA (US)

( * ) Notice: Subject to any disclaimer, the term of this patent is extended or adjusted under 35 U.S.C. 154(b) by 0 days.

(21) Appl. No.: 14/066,750

(22) Filed: Oct. 30, 2013

Related U.S. Application Data

(60) Provisional application No. 61/728,263, filed on Nov. 20, 2012, provisional application No. 61/720,045, filed on Oct. 30, 2012.

(51) Int. Cl.
| | | |
|---|---|---|
| *A61K 36/28* | (2006.01) | |
| *A61K 9/00* | (2006.01) | |
| *A61K 31/045* | (2006.01) | |

(52) U.S. Cl.
CPC .............. *A61K 9/0046* (2013.01); *A61K 31/045* (2013.01); *A61K 36/28* (2013.01)
USPC ........................................................ 424/737

(58) Field of Classification Search
CPC ...... A61K 36/28; A61K 36/484; A61K 36/00
See application file for complete search history.

(56) References Cited

U.S. PATENT DOCUMENTS

| | | | |
|---|---|---|---|
| 4,369,190 A | 1/1983 | Schulte | |
| 4,407,801 A | 10/1983 | Arnaud et al. | |
| 4,857,512 A | 8/1989 | Wagner et al. | |
| 5,064,858 A | 11/1991 | Sapse | |
| 5,376,374 A | 12/1994 | Zelaya | |
| 5,378,465 A | 1/1995 | Zeines | |
| 5,578,307 A | 11/1996 | Wunderlich et al. | |
| 5,716,961 A | 2/1998 | Sands | |
| 5,817,658 A | 10/1998 | Siegl et al. | |
| 5,863,941 A | 1/1999 | Liedtke | |
| 5,876,728 A | 3/1999 | Kass et al. | |
| 5,929,041 A | 7/1999 | Magal | |
| 6,027,716 A | 2/2000 | Levin et al. | |
| 6,039,950 A | 3/2000 | Khwaja et al. | |
| 6,093,417 A | 7/2000 | Petrus | |
| 6,096,307 A | 8/2000 | Braswell et al. | |
| 6,113,907 A | 9/2000 | Khwaja et al. | |
| 6,156,728 A | 12/2000 | Gao | |
| 6,197,305 B1 | 3/2001 | Friedman et al. | |
| 6,217,878 B1 | 4/2001 | Menon et al. | |
| 6,238,696 B1 | 5/2001 | Wang | |
| 6,379,716 B2 | 4/2002 | Santhanam et al. | |
| 6,447,815 B1 | 9/2002 | Menon et al. | |
| 6,465,442 B2 | 10/2002 | El Khoury | |
| 6,482,432 B2 | 11/2002 | Wang | |
| 6,511,683 B1 | 1/2003 | Gahler et al. | |
| 6,544,530 B1 | 4/2003 | Friedman | |
| 6,693,107 B1 | 2/2004 | Simon | |
| 6,818,761 B2 | 11/2004 | Giori et al. | |
| 6,838,092 B2 | 1/2005 | Mercati | |
| 6,881,426 B2 | 4/2005 | Giori et al. | |
| 7,135,198 B2 | 11/2006 | Frater-Schroder et al. | |
| 7,288,271 B2 | 10/2007 | Graus et al. | |
| 7,294,345 B2 | 11/2007 | Haapakumpu et al. | |
| 7,303,772 B2 | 12/2007 | Olalde Rangel et al. | |
| 7,465,723 B2 | 12/2008 | Schmutz | |
| 7,491,414 B2 | 2/2009 | Wang | |
| 7,498,360 B2 | 3/2009 | Rask-Andersen et al. | |
| 7,597,915 B2 | 10/2009 | Bombardelli | |
| 7,682,616 B2 | 3/2010 | Olalde Rangel et al. | |
| 7,829,067 B2 | 11/2010 | D'Amelio, Sr. et al. | |
| 7,871,647 B1 | 1/2011 | Paradise | |
| 7,959,953 B2 | 6/2011 | Zimmerman et al. | |
| 7,964,221 B2 | 6/2011 | Pylypchuk | |
| 7,964,224 B2 | 6/2011 | Beavers | |
| 8,025,909 B2 | 9/2011 | Jarvis et al. | |
| 8,062,680 B2 | 11/2011 | Olalde Rangel | |
| 8,075,924 B2 | 12/2011 | Loewy et al. | |
| 8,075,926 B2 | 12/2011 | Levine et al. | |
| 8,101,208 B2 | 1/2012 | Lakkis et al. | |
| 8,206,762 B2 | 6/2012 | Freund et al. | |
| 8,247,006 B2 | 8/2012 | Golio | |
| 8,268,866 B2 | 9/2012 | Guitton et al. | |
| 8,273,385 B1 | 9/2012 | Shine | |
| 2002/0009508 A1 | 1/2002 | Santhanam et al. | |
| 2002/0028258 A1 | 3/2002 | Mitscher et al. | |
| 2002/0146473 A1 | 10/2002 | Menon et al. | |
| 2003/0104076 A1 | 6/2003 | Berkulin et al. | |
| 2003/0152653 A1 | 8/2003 | Gahler et al. | |

(Continued)

FOREIGN PATENT DOCUMENTS

| | | | |
|---|---|---|---|
| WO | WO 2008104076 A1 | * | 9/2008 |
| WO | WO 2009023918 A1 | * | 2/2009 |

OTHER PUBLICATIONS

Website document entitled "Ear-Heal" (available at http://www.nativeremedies.com/products/earheal-support-ear-health.html). Downloaded from website Jan. 7, 2014.*
Barnes et al. (2005) J. Pharmacy and Pharmacology 57: 929-954.*
Barrett (2003) Phytomedicine 10: 66-86.*
Stanisavljevic et al. (2009) Chinese J. Chem. Engineering 17(3): 478-483.*
Brinkeborn et al. (1999) Phytomedicine, vol. 6(1): pp. 1-5.*
Website document entitled: "Ear drop" (available at http://en.wikipedia.org/wiki/Ear-drop). Downloaded from website Jun. 26, 2014. Archived to Sep. 13, 2006 @ www.archive.org..*
Website document entitled: "Ear infections (Otitis Media)" (available at http://www.dcnutrition.com/problems/Detail.CFM?RecordNumber=353) Downloaded from website: Jun. 20, 2014. Archived to Jul. 2, 2001 @ www.archive.org.*

*Primary Examiner* — Chris R Tate
*Assistant Examiner* — Russell Fiebig
(74) *Attorney, Agent, or Firm* — Mitchell A. Rossman; Terra Nova Patent Law, PLLC

(57) ABSTRACT

The present invention provides a method of topically treating an otological disorder in a patient in need thereof. The method includes administering topically inside an ear a therapeutically effective amount of composition including an alkyl alcohol; and an *Echinacea* tincture.

11 Claims, No Drawings

(56) References Cited

U.S. PATENT DOCUMENTS

| | | |
|---|---|---|
| 2004/0022878 A1 | 2/2004 | Giori et al. |
| 2004/0151789 A1 | 8/2004 | Levine et al. |
| 2007/0071839 A1 | 3/2007 | Bombardelli |
| 2007/0082074 A1 | 4/2007 | Wang |
| 2007/0122492 A1 | 5/2007 | Behr et al. |
| 2008/0124408 A1 | 5/2008 | Lehmann et al. |
| 2009/0285907 A1 | 11/2009 | Freund et al. |
| 2010/0303935 A1 | 12/2010 | Squires |
| 2011/0059194 A1 | 3/2011 | Lehmann et al. |
| 2011/0244041 A1 | 10/2011 | Popp |

OTHER PUBLICATIONS

Singh, Navrozedeep, "A comparison of both water and ethanol extract prepared from *Echinacea purpurea* and *Echinacea angustifolia* on the reponse to influenze A/PR/8/34 infection in mice" (2010), Graduate Theses and Dissertations, Paper 11290.*

Website document entitled: "Swimmer's ear" (available at https://www.entnet.org/content/swimmers-ear). Downloaded from website Jun. 25, 2014. Websited updated: Dec. 2010.*

\* cited by examiner

METHODS OF TOPICALLY TREATING TINNITUS AND RELATED DISORDERS

RELATED APPLICATIONS

This application claims priority to U.S. Provisional Patent Application Ser. No. 61/728,263 filed Nov. 20, 2012, and U.S. Provisional Patent Application Ser. No. 61/720,045 filed Oct. 30, 2012, which are hereby incorporated by reference in their entirety for all purposes.

BACKGROUND OF THE INVENTION

Tinnitus is the phantom sensation of hearing in the absence of external sounds. Two main types of tinnitus include (1) objective tinnitus, which is caused by sounds generated somewhere in the body; (2) subjective tinnitus, which is the perception of meaningless sounds without any physical sound being present. Objective tinnitus is rare and is caused by a sound in the body, such as turbulent flow of blood or muscle contractions in the head. Such tinnitus can be heard by an observer in contrast to subjective tinnitus, which can only be heard by the individual who has the tinnitus. Subjective tinnitus is the most prevalent type of tinnitus. Tinnitus sounds can take a variety of forms such as buzzing, ringing, or a range of other sounds.

Tinnitus often occurs as a result of dysfunction of the hearing system, such as from noise exposure, presbyacusis or from administration of specific pharmacologic agents. It can also be caused as the result of ear or head injuries, some diseases of the ear, ear infections and emotional stress. Perhaps the most common source of chronic tinnitus is exposure to loud sound. The noise causes permanent damage to the sound-sensitive cells of the cochlea, a spiral shaped organ in the inner ear. One in 10 adults have clinically significant tinnitus (regular prolonged spontaneous tinnitus lasting 5 minutes or more), and for 1 in 100 adults tinnitus severely affects their ability to lead a normal life.

There are several therapeutic approaches to alleviate tinnitus including, for example, sound therapy or sound enrichment, cognitive-behavioral therapy, repetitive transcranial magnetic stimulation, epidural cortical stimulation with implantable electrodes, and treatment using anti-depressants, anxiolytics, anesthetics, anti-convulsants, analgesics, anti-arrythmics, herbal medicines, anti-coagulants, sedative-hypnotics, anti-histaminergic compounds, anti-psychotics, anti-oxidants, vasodilators, and the like.

What is needed is a method of topically treating tinnitus and related disorders that is effective and easy to implement.

SUMMARY OF THE INVENTION

The present invention provides a method of topically treating an otological disorder in a patient in need thereof. The method includes administering topically inside an ear a therapeutically effective amount of composition including an alkyl alcohol; and an *Echinacea* tincture.

In one embodiment, the otological disorder includes tinnitus, auditory hyperesthesia, Menire's disease, endolymphatic hydrops, or a combination thereof. In one embodiment, the otological disorder is tinnitus. In one embodiment, the otological disorder includes auditory hyperesthesia. In one embodiment, the otological disorder includes Menire's disease. In one embodiment, the otological disorder includes endolymphatic hydrops.

In one embodiment, the administering topically inside an ear the therapeutically effective amount of composition is performed about every 24 hours for about 3 times followed by 48 hours of rest. In one embodiment, the administering topically inside an ear the therapeutically effective amount of composition is performed about every 24 hours for about 3 times followed by 48 hours of rest on a continuous basis.

In one embodiment, the method further includes having the patient lie on their side from about five to about ten minutes to allow the composition to soak into the ear. In one embodiment, the method further includes having the patient close off their mouth and nose and blow until their ears pop and swallow to unpop their ears from about one to about five times. In one embodiment, the method further includes having the patient close off their mouth and nose and blow until their ears pop and swallow to unpop their ears from about three to about four times.

In one embodiment, the alkyl alcohol includes methanol, ethanol, 1-propanol, 2-propanol, 1-butanol, 2-methanol-1-propanol, iso-butanol, sec-butanol, tert-butanol, 1-pentanol, 2-pentanol, 3-pentanol, 2-methanol-2-butanol, 3-methanol-2-butanol, 3-methanol-1-butanol, 2-methanol-1-butanol, 1-hexanol, 2-hexanol, 3-hexanol, 2-methanol-2-pentanol, 3-methanol-2-pentanol, 4-methanol-2-pentanol, 3-methanol-3-pentanol, 2-methanol-3-pentanol, 2,3-dimethanol-2-butanol, and 3,3-dimethanol-2-butanol, or a combination thereof.

In one embodiment, the alkyl alcohol includes ethanol. In one embodiment, the alkyl alcohol includes isopropanol.

In one embodiment, the composition includes from about 1 percent by weight (wt-%) to about 50 percent by weight (wt-%) alkyl alcohol. In one embodiment, the composition includes from about 2 percent by weight (wt-%) to about 30 percent by weight (wt-%) alkyl alcohol. In one embodiment, the composition includes from about 3 percent by weight (wt-%) to about 25 percent by weight (wt-%) alkyl alcohol. In one embodiment, the composition includes about 3 percent by weight (wt-%) alkyl alcohol. In one embodiment, the composition includes about 10 percent by weight (wt-%) alkyl alcohol. In one embodiment, the composition includes about 23 percent by weight (wt-%) alkyl alcohol.

In one embodiment, the composition includes from about 50 percent by weight (wt-%) to about 99 percent by weight (wt-%) *Echinacea* tincture. In one embodiment, the composition includes from about 65 percent by weight (wt-%) to about 99 percent by weight (wt-%) *Echinacea* tincture. In one embodiment, the composition includes from about 75 percent by weight (wt-%) to about 99 percent by weight (wt-%) *Echinacea* tincture.

In one embodiment, the composition includes about 77 percent by weight (wt-%) *Echinacea* tincture. In one embodiment, the composition includes about 90 percent by weight (wt-%) *Echinacea* tincture. In one embodiment, the composition includes about 97 percent by weight (wt-%) *Echinacea* tincture.

In one embodiment, the composition includes about 3 percent by weight (wt-%) alkyl alcohol and about 97 percent by weight (wt-%) *Echinacea* tincture. In one embodiment, the composition includes about 10 percent by weight (wt-%) alkyl alcohol and about 90 percent by weight (wt-%) *Echinacea* tincture. In one embodiment, the composition includes about 23 percent by weight (wt-%) alkyl alcohol and about 77 percent by weight (wt-%) *Echinacea* tincture.

In one embodiment, the composition includes about 3 percent by weight (wt-%) ethanol and about 97 percent by weight (wt-%) *Echinacea* tincture. In one embodiment, the composition includes about 10 percent by weight (wt-%) ethanol and about 90 percent by weight (wt-%) *Echinacea* tincture. In one embodiment, the composition includes about 23 percent by weight (wt-%) ethanol and about 77 percent by weight (wt-%) *Echinacea* tincture.

In one embodiment, the composition includes from about 3 percent to about 23 percent by weight (wt-%) ethanol and from about 77 percent to about 97 percent by weight (wt-%) *Echinacea* tincture.

In one embodiment, the composition includes from about 1 percent to about 40 percent by weight (wt-%) ethanol and from about 60 percent to about 99 percent by weight (wt-%) *Echinacea* tincture.

In one embodiment, the *Echinacea* tincture is prepared by grinding organic *Echinacea* roots and stems into a powder, wherein the powder is extracted with water for about 36 hours and filtered to remove the solid matter. In one embodiment, the *Echinacea* tincture is prepared by grinding from about 20 percent by weight (wt-%) organic *Echinacea* roots and stems into a powder, wherein the powder is extracted in about 80 percent by weight (wt-%) water for about 36 hours and filtered to remove the solid matter. In one embodiment, the *Echinacea* tincture is prepared by grinding from about 30 percent by weight (wt-%) organic *Echinacea* roots and stems into a powder, wherein the powder is extracted in about 70 percent by weight (wt-%) water for about 36 hours and filtered to remove the solid matter.

In one embodiment, the *Echinacea* tincture is prepared by grinding about 33 percent by weight (wt-%) organic *Echinacea* roots and stems into a powder, wherein the powder is extracted in about 66 percent by weight (wt-%) water for about 36 hours and filtered to remove the solid matter. In one embodiment, the *Echinacea* tincture is prepared by grinding from about 20 percent by weight (wt-%) organic *Echinacea* roots and stems into a powder, wherein the powder is extracted in about 80 percent by weight (wt-%) water for about 36 hours in the presence of sunlight and filtered to remove the solid matter. In one embodiment, the *Echinacea* tincture is prepared by grinding from about 30 percent by weight (wt-%) organic *Echinacea* roots and stems into a powder, wherein the powder is extracted in about 70 percent by weight (wt-%) water for about 36 hours in the presence of sunlight and filtered to remove the solid matter. In one embodiment, the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter.

In one embodiment, the *Echinacea* tincture is prepared by grinding *Echinacea* roots and stems derived from *Echinacea angustifolia, Echinacea atrorubens, Echinacea laevigata, Echinacea pallida, Echinacea paradoxa, Echinacea purpurea, Echinacea sanguinea, Echinacea simulata, Echinacea tennesseensis*, or a combination thereof.

The present invention provides a method of topically treating tinnitus in a patient in need thereof. The method includes administering topically inside an ear a therapeutically effective amount of composition including: ethanol; and an *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

The present invention provides a method of topically treating tinnitus in a patient in need thereof. The method includes: administering topically inside an ear a therapeutically effective amount of composition including: from about 3 percent to about 23 percent by weight (wt-%) ethanol, and from about 77 percent to about 97 percent by weight (wt-%) *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

The present invention provides a method of topically treating tinnitus in a patient in need thereof. The method includes: administering topically inside an ear a therapeutically effective amount of composition including: from about 1 percent to about 40 percent by weight (wt-%) ethanol, and from about 60 percent to about 99 percent by weight (wt-%) *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

The present invention provides a method of topically treating tinnitus in a patient in need thereof. The method includes: administering topically inside an ear a therapeutically effective amount of composition including: from about 3 percent to about 23 percent by weight (wt-%) ethanol, and from about 77 percent to about 97 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times.

The present invention provides a method of topically treating tinnitus in a patient in need thereof. The method includes: administering topically inside an ear a therapeutically effective amount of composition including: from about 3 percent to about 23 percent by weight (wt-%) ethanol, and from about 77 percent to about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition consisting essentially of: from about 3 percent to about 23 percent by weight (wt-%) ethanol, and from about 77 percent to about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition consisting of: from about 3 percent to about 23 percent by weight (wt-%) ethanol, and from about 77 percent to about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition including: about 3 percent by weight (wt-%) ethanol, and about 97 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition including: about 10 percent by weight (wt-%) ethanol, and about 90 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition including: about 23 percent by weight (wt-%) ethanol, and about 77 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition including: about 3 percent by weight (wt-%) ethanol, and about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition including: about 10 percent by weight (wt-%) ethanol, and about 90 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition including: about 23 percent by weight (wt-%) ethanol, and about 77 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating tinnitus in a patient in need thereof. The method includes: administering topically inside an ear a therapeutically effective amount of composition including: ethanol or isopropanol; and an *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

In one embodiment, the administering topically inside an ear the therapeutically effective amount of composition is performed about every 24 hours for about 3 times followed by 48 hours of rest. In one embodiment, the administering topically inside an ear the therapeutically effective amount of composition is performed about every 24 hours for about 3 times followed by 48 hours of rest on a continuous basis. In one embodiment, the composition includes about 3 percent by weight (wt-%) ethanol or isopropanol and about 97 percent by weight (wt-%) *Echinacea* tincture.

In one embodiment, the composition includes about 10 percent by weight (wt-%) ethanol or isopropanol and about 90 percent by weight (wt-%) *Echinacea* tincture. In one embodiment, the composition includes about 23 percent by weight (wt-%) ethanol or isopropanol and about 77 percent by weight (wt-%) *Echinacea* tincture. In one embodiment, the composition includes from about 3 percent to about 23 percent by weight (wt-%) ethanol or isopropanol and from about 77 percent to about 97 percent by weight (wt-%) *Echinacea* tincture.

The present invention provides a method of topically treating an otological disorder in a patient in need thereof. The method includes: administering topically inside an ear a therapeutically effective amount of composition including: an aprotic solvent or a protic solvent; and an *Echinacea* tincture, wherein the otological disorder includes ear pain, excess or impacted cerumen, blockage or obstruction of the Eustachian tube, common ear infections, swimmer's ear, menierere's disease, glue ear, jaw hyperactivity, neck arthritis, mastoiditis, cholesteatoma, Otitis media, Otitis externa, or a combination thereof.

The present invention provides a method of topically treating ear pain in a patient in need thereof. The method includes: administering topically inside an ear a therapeutically effective amount of composition including: an alkyl alcohol; and an *Echinacea* tincture. The present invention provides a method of topically treating ear pain in a patient in need thereof. The method includes: administering topically inside an ear a therapeutically effective amount of composition including: ethanol; and an *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

The present invention provides a method of topically treating ear pain in a patient in need thereof. The method includes: administering topically inside an ear a therapeutically effective amount of composition including: from about 3 percent to about 23 percent by weight (wt-%) ethanol, and from about 77 percent to about 97 percent by weight (wt-%) *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

The present invention provides a method of topically treating ear pain in a patient in need thereof. The method includes: administering topically inside an ear a therapeutically effective amount of composition including: from about 1 percent to about 40 percent by weight (wt-%) ethanol, and from about 60 percent to about 99 percent by weight (wt-%) *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

The present invention provides a method of topically treating ear pain in a patient in need thereof. The method includes: administering topically inside an ear a therapeutically effective amount of composition including: from about 3 percent to about 23 percent by weight (wt-%) ethanol, and from about 77 percent to about 97 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times.

The present invention provides a method of topically treating ear pain in a patient in need thereof. The method includes: administering topically inside an ear a therapeutically effective amount of composition including: from about 3 percent to about 23 percent by weight (wt-%) ethanol, and from about 77 percent to about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition consisting essentially of: from about 3 percent to about 23 percent by weight (wt-%) ethanol, and from about 77 percent to about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition consisting of: from about 3 percent to about 23 percent by weight (wt-%) ethanol, and from about 77 percent to about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition including: about 3 percent by weight (wt-%) ethanol, and about 97 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition including: about 10 percent by weight (wt-%) ethanol, and about 90 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition including: about 23 percent by weight (wt-%) ethanol, and about 77 percent by weight (wt-%) *Echinacea* tincture; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition including: about 3 percent by weight (wt-%) ethanol, and about 97 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition including: about 10 percent by weight (wt-%) ethanol, and about 90 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition including: about 23 percent by weight (wt-%) ethanol, and about 77 percent by weight (wt-%) *Echinacea* tincture, wherein the *Echinacea* tincture is prepared by grinding about 33 percent by weight (wt-%) organic *Echinacea* roots and stems into a powder, wherein the powder is extracted in about 66 percent by weight (wt-%) water for about 36 hours in the presence of sunlight and filtered to remove the solid matter; having the patient lie on their side from about five to about ten minutes to allow the composition to soak into the ear, and having the patient close off their mouth and nose and blow until their ears pop and swallow to unpop their ears from about one to about five times, wherein the administering topically inside an ear the therapeutically effective amount of composition is performed about every 24 hours for about 3 times followed by 48 hours of rest.

The present invention provides a method of topically treating ear pain in a patient in need thereof. The method includes: administering topically inside an ear a therapeutically effective amount of composition including: ethanol or isopropanol; and an *Echinacea* tincture; optionally having the patient lie on their side from about five to about ten minutes to allow the composition to soak into the ear, and optionally having the patient close off their mouth and nose and blow until their ears pop and swallow to unpop their ears from about one to about five times.

The present invention provides a method of topically treating ear pain in a patient in need thereof. The method includes: administering topically inside an ear a therapeutically effective amount of composition including: an aprotic solvent or a protic solvent; and an *Echinacea* tincture.

DETAILED DESCRIPTION OF THE INVENTION

One of ordinary skill in the art would readily appreciate that the formulations and methods described herein can be prepared and practiced by applying known procedures in the pharmaceutical arts. These include, for example, unless otherwise indicated, conventional techniques of pharmaceutical sciences including pharmaceutical dosage form design, drug development, pharmacology, of organic chemistry, and polymer sciences. See generally, for example, *Remington: The Science and Practice of Pharmacy*, 21$^{st}$ edition, Lippincott, Williams & Wilkins, (2005).

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993, *The American Heritage Dictionary of the English Language*, Houghton Mifflin, Boston Mass., 1981, and *Hawley's Condensed Chemical Dictionary*, 14$^{th}$ edition, Wiley Europe, 2002.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "administration" refers to a method of placing a composition in a desired site.

As used herein, the term "alcohol" refers to a compound of a general formula ROH.

As used herein, the term "alkyl" refers to a $C_1$-$C_{18}$ hydrocarbon containing normal, secondary, tertiary or cyclic carbon atoms.

As used herein, the term "aprotic solvent" refers to polar solvents of moderately high dielectric constant which do not contain an acidic hydrogen. Examples of common aprotic solvents are dimethylsulfoxide (DMSO), dimethylformamide, sulfolane, tetrahydrofuran, diethyl ether, methyl-t-butyl ether, or 1,2-dimethoxyethane.

As used herein, the phrase "*Echinacea*" refers to a genus consisting of nine species of flowering plants, which are all native to eastern and central North America, including, for example, *Echinacea angustifolia, Echinacea atrorubens, Echinacea laevigata, Echinacea pallida, Echinacea paradoxa, Echinacea purpurea, Echinacea sanguinea, Echinacea simulata*, and *Echinacea tennesseensis*, or a combination thereof. Both roots, aerial parts of the plants, and combinations thereof may be used.

As used herein, the terms "include," "for example," "such as," and the like are used illustratively and are not intended to limit the present invention.

As used herein, the term "mammal" refers to any of a class of warm-blooded higher vertebrates that nourish their young with milk secreted by mammary glands and have skin usually more or less covered with hair, and non-exclusively includes humans and non-human primates, their children, including neonates and adolescents, both male and female, livestock species, such as horses, cattle, sheep, and goats, and research and domestic species, including dogs, cats, mice, rats, guinea pigs, and rabbits.

As used herein, the terms "optional" or "optionally" mean that the subsequently described event or condition may but need not occur, and that the description includes instances where the event or condition occurs and instances in which it does not.

As used herein, the term "patient" refers to a warm-blooded animal, and preferably a mammal, for example, a cat, dog, horse, cow, pig, mouse, rat, or primate, including a human.

As used herein, the term "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio. Several pharmaceutically acceptable ingredients are known in the art and official publications such as *The United States Pharmacoepia* describe the analytical criteria to assess the pharmaceutical acceptability of numerous ingredients of interest.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "preventing" or "prevention" refers to suppressing or reducing the likelihood of acquiring tinnitus (i.e., causing at least one of the clinical symptoms of tinnitus not to develop in a patient that may be exposed to a factor believed to cause tinnitus or predisposed to tinnitus but does not yet experience or display symptoms of tinnitus).

As used herein, the term "protic solvent" refers to a solvent containing hydrogen that is attached to oxygen, and hence is appreciably acidic. Common protic solvents include such solvents as water, methanol, ethanol, 2-propanol, and 1-butanol.

As used herein, the term "skin" refers to the external tissue layer in humans and animals consisting of epidermis and dermis.

As used herein, the term "therapeutically effective amount" is intended to include an amount of a compound described herein, or an amount of the combination of compounds described herein, e.g., to treat or prevent the disease or disorder, or to treat the symptoms of the disease or disorder, in a host. The combination of compounds is preferably a synergistic combination. Synergy, as described for example by Chou and Talalay, *Adv. Enzyme Regul.*, 22:27 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

As used herein, the terms "therapy," and "therapeutic" refer to either "treatment" or "prevention," thus, agents that either treat damage or prevent damage are "therapeutic."

As used herein, the term "tinnitus" refers to all manifestations of subjective and objective tinnitus as well as acute, sub-acute and chronic forms.

As used herein, the term "topically" refers to application of the compositions of the present invention to the surface of the skin and mucosal cells and tissues (e.g., alveolar, buccal, lingual, sublingual, masticatory, or nasal mucosa, and other tissues and cells, which line hollow organs or body cavities).

As used herein, the terms "treating" or "treat" or "treatment" refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

As used herein, the terms "treating" or "treatment" of tinnitus refer to arresting or ameliorating tinnitus, or at least one of the clinical symptoms of tinnitus, reducing the risk of acquiring tinnitus, or at least one of the clinical symptoms of tinnitus, reducing the development of tinnitus or at least one of the clinical symptoms of tinnitus, or reducing the risk of developing tinnitus, or at least one of the clinical symptoms of tinnitus.

As used herein, the terms "treating" or "treatment" also refer to inhibiting tinnitus, either physically, (e.g., suppressing, reducing, or stabilizing a discernible symptom), physiologically, (e.g., suppressing, reducing, or stabilizing a physical parameter), or both, and to inhibiting at least one physical parameter that may or may not be discernible to the patient. In certain embodiments, the terms "treating" or "treatment" refer to delaying the onset of tinnitus or at least one or more symptoms thereof in a patient, which may be exposed to a factor believed to cause tinnitus or predisposed to tinnitus even though that patient does not yet experience or display symptoms of tinnitus.

As used herein, the terms "treating" and "treatment" and "to treat" refer to preventing, reducing, or eliminating tinnitus and/or the accompanying symptoms of tinnitus in a patient. Treatment refers to any indicia of success in prevention, reduction, elimination, or amelioration of tinnitus, including any objective or subjective parameter such as abatement, remission, diminishing of symptoms, prevention, or lessening of tinnitus symptoms or making the condition more tolerable to the patient, making the tinnitus less debilitating, or improving a patient's physical or mental well-being. For example, success of treatment by methods of treating tinnitus provided by the present disclosure may be measured by comparing the frequency and/or severity of tinnitus before treatment with the compositions described herein is initiated, with the frequency and/or severity of tinnitus following the initiation of treatment with the compositions described herein. The prevention, treatment, or amelioration of tinnitus symptoms may be based on objective or subjective parameters, including the results of a physical examination, or personal interview regarding symptom severity and quality of life, or any other appropriate means known in the art.

As used herein, "µg" denotes microgram, "mg" denotes milligram, "g" denotes gram, "µL" denotes microliter, "mL" denotes milliliter, "L" denotes liter, "nM" denotes nanomolar, "µM" denotes micromolar, "mM" denotes millimolar, "M" denotes molar, and "nm" denotes nanometer.

Concentrations, amounts, etc., of various components are often presented in a range format throughout this disclosure. The description in range format is merely for convenience and brevity and should not be construed as an inflexible limitation on the scope of the claimed invention. Accordingly, the description of a range should be considered to have specifically disclosed all the possible sub ranges as well as individual numerical values within that range. For example, description of a range such as 1% to 8% should be considered to have specifically disclosed sub ranges such as 1% to 7%, 2% to 8%, 2% to 6%, 3% to 6%, 4% to 8%, 3% to 8% etc., as well as individual numbers within that range, such as, 2%, 5%, 7% etc. This construction applies regardless of the breadth of the range and in all contexts throughout this disclosure.

It will be understood that, although the terms first, second, etc. May be used herein to describe various elements, these elements should not be limited by these terms. These terms are only used to distinguish one element from another. For example, a first element could be termed a second element, and, similarly, a second element could be termed a first element without departing from the teachings of the disclosure.

The present invention provides a method of topically treating an otological disorder in a patient in need thereof. The method includes administering topically inside an ear a therapeutically effective amount of composition including an alkyl alcohol; and an *Echinacea* tincture. Typically, the otological disorder may include tinnitus, auditory hyperesthesia, Menire's disease, endolymphatic hydrops, or a combination thereof. Preferably, the otological disorder is tinnitus.

The administering topically inside an ear a therapeutically effective amount of composition is performed about every 24 hours for about 3 times followed by 48 hours of rest, preferably about every 24 hours for about 3 times followed by 48 hours of rest on a continuous basis.

The method may also include having the patient lie on their side from about five to about ten minutes to allow the composition to soak into the ear, having the patient close off their mouth and nose and blow until their ears pop and swallow to unpop their ears from about one to about five times, preferably, having the patient close off their mouth and nose and blow until their ears pop and swallow to unpop their ears from about three to about four times.

The alkyl alcohol may include, for example, methanol, ethanol, 1-propanol, 2-propanol, 1-butanol, 2-methanol-1 propanol, iso-butanol, sec-butanol, tert-butanol, 1-pentanol, 2-pentanol, 3-pentanol, 2-methanol-2-butanol, 3-methanol-2-butanol, 3-methanol-1-butanol, 2-methanol-1-butanol, 1-hexanol, 2-hexanol, 3-hexanol, 2-methanol-2-pentanol, 3-methanol-2-pentanol, 4-methanol-2-pentanol, 3-methanol-3-pentanol, 2-methanol-3-pentanol, 2,3-dimethanol-2-butanol, and 3,3-dimethanol-2-butanol, or a combination thereof. Preferably, the alkyl alcohol is ethanol.

The composition may include, for example, from about 1 percent by weight (wt-%) to about 50 percent by weight (wt-%) alkyl alcohol, from about 2 percent by weight (wt-%) to about 30 percent by weight (wt-%) alkyl alcohol, or from about 3 percent by weight (wt-%) to about 25 percent by weight (wt-%) alkyl alcohol.

Preferably, the composition may include, for example, about 3 percent by weight (wt-%) alkyl alcohol, about 10 percent by weight (wt-%) alkyl alcohol, or about 23 percent by weight (wt-%) alkyl alcohol.

The composition may include, for example, from about 50 percent by weight (wt-%) to about 99 percent by weight (wt-%) *Echinacea* tincture, from about 65 percent by weight (wt-%) to about 99 percent by weight (wt-%) *Echinacea* tincture, or from about 75 percent by weight (wt-%) to about 99 percent by weight (wt-%) *Echinacea* tincture.

Preferably, the composition may include, for example, about 77 percent by weight (wt-%) *Echinacea* tincture, about 90 percent by weight (wt-%) *Echinacea* tincture, or about 97 percent by weight (wt-%) *Echinacea* tincture.

The composition may include, for example, about 3 percent by weight (wt-%) alkyl alcohol and about 97 percent by weight (wt-%) *Echinacea* tincture, about 10 percent by weight (wt-%) alkyl alcohol and about 90 percent by weight (wt-%) *Echinacea* tincture, or about 23 percent by weight (wt-%) alkyl alcohol and about 77 percent by weight (wt-%) *Echinacea* tincture.

Preferably, the composition may include, for example, about 3 percent by weight (wt-%) ethanol and about 97 percent by weight (wt-%) *Echinacea* tincture, about 10 percent by weight (wt-%) ethanol and about 90 percent by weight (wt-%) *Echinacea* tincture, or about 23 percent by weight (wt-%) ethanol and about 77 percent by weight (wt-%) *Echinacea* tincture.

The composition may include, for example, from about 3 percent to about 23 percent by weight (wt-%) ethanol and from about 77 percent to about 97 percent by weight (wt-%) *Echinacea* tincture.

The *Echinacea* tincture maybe prepared by grinding, for example, organic *Echinacea* roots and stems into a powder, wherein the powder is extracted with water for about 36 hours and filtered to remove the solid matter, or about 20 percent by weight (wt-%) organic *Echinacea* roots and stems into a powder, wherein the powder is extracted in about 80 percent by weight (wt-%) water for about 36 hours and filtered to remove the solid matter, or from about 30 percent by weight (wt-%) organic *Echinacea* roots and stems into a powder, wherein the powder is extracted in about 70 percent by weight (wt-%) water for about 36 hours and filtered to remove the solid matter, or about 33 percent by weight (wt-%) organic *Echinacea* roots and stems into a powder, wherein the powder is extracted in about 66 percent by weight (wt-%) water for about 36 hours and filtered to remove the solid matter.

Preferably, *Echinacea* tincture maybe prepared by grinding, for example, about 20 percent by weight (wt-%) organic *Echinacea* roots and stems into a powder, wherein the powder is extracted in about 80 percent by weight (wt-%) water for about 36 hours in the presence of sunlight and filtered to remove the solid matter, or about 30 percent by weight (wt-%) organic *Echinacea* roots and stems into a powder, wherein the powder is extracted in about 70 percent by weight (wt-%) water for about 36 hours in the presence of sunlight and filtered to remove the solid matter, or about 33 percent by weight (wt-%) organic *Echinacea* roots and stems into a powder, wherein the powder is extracted in about 66 percent by weight (wt-%) water for about 36 hours in the presence of sunlight and filtered to remove the solid matter.

The *Echinacea* tincture is typically prepared by grinding, for example. *Echinacea* roots and stems derived from *Echinacea angustifolia, Echinacea atrorubens, Echinacea laevigata, Echinacea pallida, Echinacea paradoxa, Echinacea purpurea, Echinacea sanguinea, Echinacea simulata, Echinacea tennesseensis*, or a combination thereof.

The composition for the topical treatment of tinnitus in humans may also include one or more optional ingredients, for example, anti-viral agents, palliative agents, anti-itch agents, anti-microbial and anti-fungal agents, non-steroid cosmetic soothing agents, steroids, skin conditioning agents, emollients, humectants, odorants, preservatives, solvents, thickening, stiffening and suspending agents, other agents, and combinations thereof.

The composition for the topical treatment of tinnitus in humans may be topically applied for a period of time of about one month, about two months, about three months, about four months, about five months, about six months, about seven months, about eight months, about nine months, about ten months, about eleven months, about one year, about 1.5 years, about 2 years, about 2.5 years, about 3 years, about 3.5 years, about 4 years, about 4.5 years, and about 5 years.

Dosage forms of the composition for the topical treatment of tinnitus in humans include, for example, ointments, creams, emulsions, liquids, lotions, gels, aerosols, shampoos, pastes, or foams. Preferably, the composition for the topical treatment of tinnitus in humans is a liquid that can be easily applied to the ear.

The compositions provided herein may be formulated in a unit dosage form. A unit dosage form refers to a physically discrete unit suitable as a unitary dose for patients undergoing treatment, with each unit containing a predetermined quantity of a composition described herein calculated to produce the intended therapeutic effect. A unit dosage form may be for a single daily dose, 1 to 2 times per day, or one of multiple daily doses, for example, 2 to 4 times per day. When multiple daily doses are used, the unit dosage may be the same or different for each dose. One or more dosage forms may comprise a dose, which may be administered to a patient at a single point in time or during a time interval.

A topical dosage form may also be in the form of an insert. An insert comprises a matrix containing a composition described herein. For example, the matrix may be a polymer and the composition described herein may be dispersed within the polymer matrix and/or bonded to the polymer matrix.

The compositions described may have a viscosity that is suitable for the selected route of administration. For example, an eardrop may have a viscosity from about 1,000 centipoise to about 30,000 centipoise. A viscous solution or ribbon form for otic administration may have a viscosity from about 30,000 centipoise to about 100,000 centipoise.

The invention should now be illustrated with the following non-limiting examples.

EXAMPLES

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

| DESCRIPTIONS AND SOURCES OF MATERIALS | |
|---|---|
| Description of Material | Source of Material |
| *Echinacea* roots and stems | Herb Pharm, LLC Williams, OR, USA |

Example 1

Preparation of *Echinacea* Tincture

About 33 grams of organic *Echinacea* roots and stems were ground up using a mortar and pestle to afford a fine powder. The powder was added to a beaker containing about 66 grams of water. The mixture was placed in the sun for about 36 hours at about room temperature. The solids are filtered to afford the *Echinacea* tincture.

Example 2

Preparation of Tinnitus Composition

To about 23 grams of ethanol (95%) was added about 77 grams of *Echinacea* tincture prepared in Example 1 and stirred at about room temperature to form a high-strength formulation.

Example 3

Preparation of Tinnitus Composition

To about 10 grams of ethanol (95%) was added about 90 grams of *Echinacea* tincture prepared in Example 1 and stirred at about room temperature to form a medium-strength formulation.

Example 4

Preparation of Tinnitus Composition

To about 3 grams of ethanol (95%) was added about 97 grams of *Echinacea* tincture prepared in Example 1 and stirred at about room temperature to form a mild-strength formulation.

Example 5

Treatment of Tinnitus

A patient suffering from tinnitus was laid on their side and about ½ dropper (30 drops) of the mild-strength formulation prepared in Example 4 was added to one ear. The composition was allowed to soak into the ear for about six to about ten minutes. The patient pinched their nose, closed their mouth, and lightly blowed until their ears popped. The patient swallowed to unpop their ears. The patient repeated the popping and unpopping their ears for about three to about four times. The patient placed a paper tissue over their ear and sat up to allow the composition to drain from the one ear. The patient repeated the procedure on their second ear and then goes to sleep.

The patient repeated the above procedure for the next two nights followed by two nights without the treatment to complete one treatment cycle. The patient repeated the treatment cycle three times and found that their tinnitus had disappeared.

Example 6

Preparation of Tinnitus Composition

To about 23 grams of isopropanol is added about 77 grams of *Echinacea* tincture prepared in Example 1 and stirred at about room temperature to form a high-strength formulation.

Example 7

Preparation of Tinnitus Composition

To about 10 grams of isopropanol is added about 90 grams of *Echinacea* tincture prepared in Example 1 and stirred at about room temperature to form a medium-strength formulation.

Example 8

Preparation of Tinnitus Composition

To about 3 grams of isopropanol is added about 97 grams of *Echinacea* tincture prepared in Example 1 and stirred at about room temperature to form a mild-strength formulation.

Example 9

Treatment of Tinnitus

A patient suffering from tinnitus is laid on their side and about ½ dropper of the mild-strength formulation prepared in Example 8 is added to one ear. The composition is allowed to soak into the ear for about six to about ten minutes. The patient pinches their nose, closes their mouth, and lightly blows until their ears pops. The patient swallows to unpop their ears. The patient repeated the popping and unpopping their ears for about three to about four times. The patient places a paper tissue over their ear and sits up to allow the composition to drain from the one ear. The patient repeats the procedure on their second ear and goes to sleep. The patient repeats the above procedure for the next two nights followed by two nights without the treatment to complete one treatment cycle.

In the claims provided herein, the steps specified to be taken in a claimed method or process may be carried out in any order without departing from the principles of the invention, except when a temporal or operational sequence is explicitly defined by claim language. Recitation in a claim to the effect that first a step is performed then several other steps are performed shall be taken to mean that the first step is performed before any of the other steps, but the other steps may be performed in any sequence unless a sequence is further specified within the other steps. For example, claim elements that recite "first A, then B, C, and D, and lastly E" shall be construed to mean step A must be first, step E must be last, but steps B, C, and D may be carried out in any sequence between steps A and E and the process of that sequence will still fall within the four corners of the claim.

Furthermore, in the claims provided herein, specified steps may be carried out concurrently unless explicit claim language requires that they be carried out separately or as parts of different processing operations. For example, a claimed step of doing X and a claimed step of doing Y may be conducted simultaneously within a single operation, and the resulting process will be covered by the claim. Thus, a step of doing X, a step of doing Y, and a step of doing Z may be conducted simultaneously within a single process step, or in two separate process steps, or in three separate process steps, and that process will still fall within the four corners of a claim that recites those three steps.

Similarly, except as explicitly required by claim language, a single substance or component may meet more than a single functional requirement, provided that the single substance fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicant reserves the right to physically incorporate into this specification any and all materials and information from any such patents, applications, publications, scientific articles, web sites, electronically available information, and other referenced materials or documents. Applicant reserves the right to physically incorporate into any part of this document, including any part of the written description, the claims referred to above including but not limited to any original claims.

What is claimed is:

1. A method of topically treating tinnitus in a patient in need thereof comprising:
   administering topically inside an ear a therapeutically effective amount of a composition comprising:
      from about 3 percent to about 23 percent by weight (wt-%) ethanol;
      from about 77 percent to about 97 percent by weight (wt-%) *Echinacea* extract, and
         wherein the *Echinacea* extract is prepared by grinding organic *Echinacea* roots and stems into a powder, and
         extracting the powder with water for about 36 hours in the presence of sunlight and filtered to remove the solid matter, and wherein the ratio of the powder to water is about 1:2 (wt:wt).

2. The method of claim 1, wherein the administering is performed about every 24 hours for about 3 times followed by 48 hours of rest.

3. The method of claim 1, further comprising having the patient lie on their side from about five to about ten minutes to allow the composition to soak into the ear.

4. The method of claim 1, further comprising having the patient lie on their side from about five to about ten minutes to allow the composition to soak into the ear, close off their mouth and nose, blow until their ears pop, and swallow to unpop their ears from about one to about five times.

5. A method of topically treating tinnitus in a patient in need thereof comprising:
   administering topically inside an ear a therapeutically effective amount of a composition consisting essentially of:
      from about 3 percent to about 23 percent by weight (wt-%) ethanol;
      from about 77 percent to about 97 percent by weight (wt-%) *Echinacea* extract,
         wherein the *Echinacea* extract is prepared by grinding organic *Echinacea* roots and stems into a powder, and
         extracting the powder with water for about 36 hours in the presence of sunlight and filtered to remove the solid matter, and wherein the ratio of the powder to water is about 1:2 (wt:wt).

6. The method of claim 5, wherein the administering topically inside the ear the therapeutically effective amount of composition is performed about every 24 hours for about 3 times followed by 48 hours of rest.

7. The method of claim 5, wherein the method further comprising having the patient lie on their side from about five to about ten minutes to allow the composition to soak into the ear.

8. The method of claim 5, wherein the method further comprising having the patient lie on their side from about five to about ten minutes to allow the composition to soak into the ear, close off their mouth and nose, blow until their ears pop, and swallow to unpop their ears from about one to about five times.

9. The method of claim 5, wherein the composition consists essentially of:
   about 23 percent by weight (wt-%) ethanol, and
   about 78 percent by weight (wt-%) *Echinacea* extract.

10. The method of claim 5, wherein the composition consists essentially of:
    about 10 percent by weight (wt-%) ethanol, and
    about 90 percent by weight (wt-%) *Echinacea* extract.

11. The method of claim 5, wherein the composition consists essentially of:
    about 3 percent by weight (wt-%) ethanol, and
    about 97 percent by weight (wt-%) *Echinacea* extract.

* * * * *

UNITED STATES PATENT AND TRADEMARK OFFICE
CERTIFICATE OF CORRECTION

| | | |
|---|---|---|
| PATENT NO. | : 8,920,855 B1 | Page 1 of 2 |
| APPLICATION NO. | : 14/066750 | |
| DATED | : December 30, 2014 | |
| INVENTOR(S) | : Charles Irmiter | |

It is certified that error appears in the above-identified patent and that said Letters Patent is hereby corrected as shown below:

On the Title Page

Delete title page and substitute therefore with the attached title page consisting of the corrected assignee's name.

Signed and Sealed this
Twenty-fourth Day of March, 2015

Michelle K. Lee
*Director of the United States Patent and Trademark Office*

(12) United States Patent
Irmiter

(10) Patent No.: US 8,920,855 B1
(45) Date of Patent: Dec. 30, 2014

(54) METHODS OF TOPICALLY TREATING TINNITUS AND RELATED DISORDERS

(71) Applicant: Charles Irmiter, Richfield, MN (US)

(72) Inventor: Charles Irmiter, Richfield, MN (US)

(73) Assignee: Setem Health, Inc. Los Angeles, CA (US)

(*) Notice: Subject to any disclaimer, the term of this patent is extended or adjusted under 35 U.S.C. 154(b) by 0 days.

(21) Appl. No.: 14/066,750

(22) Filed: Oct. 30, 2013

Related U.S. Application Data

(60) Provisional application No. 61/728,263, filed on Nov. 20, 2012, provisional application No. 61/720,045, filed on Oct. 30, 2012.

(51) Int. Cl.
| | | |
|---|---|---|
| *A61K 36/28* | (2006.01) | |
| *A61K 9/00* | (2006.01) | |
| *A61K 31/045* | (2006.01) | |

(52) U.S. Cl.
CPC ............ *A61K 9/0046* (2013.01); *A61K 31/045* (2013.01); *A61K 36/28* (2013.01)
USPC .................................................... 424/737

(58) Field of Classification Search
CPC ...... A61K 36/28; A61K 36/484; A61K 36/00
See application file for complete search history.

(56) References Cited

U.S. PATENT DOCUMENTS

| | | |
|---|---|---|
| 4,369,190 A | 1/1983 | Schulte |
| 4,407,801 A | 10/1983 | Arnaud et al. |
| 4,857,512 A | 8/1989 | Wagner et al. |
| 5,064,858 A | 11/1991 | Sapse |
| 5,376,374 A | 12/1994 | Zelaya |
| 5,378,465 A | 1/1995 | Zeines |
| 5,578,307 A | 11/1996 | Wunderlich et al. |
| 5,716,961 A | 2/1998 | Sands |
| 5,817,658 A | 10/1998 | Siegl et al. |
| 5,863,941 A | 1/1999 | Liedtke |
| 5,876,728 A | 3/1999 | Kass et al. |
| 5,929,041 A | 7/1999 | Magal |
| 6,027,716 A | 2/2000 | Levin et al. |
| 6,039,950 A | 3/2000 | Khwaja et al. |
| 6,093,417 A | 7/2000 | Petrus |
| 6,096,307 A | 8/2000 | Braswell et al. |
| 6,113,907 A | 9/2000 | Khwaja et al. |
| 6,156,728 A | 12/2000 | Gao |
| 6,197,305 B1 | 3/2001 | Friedman et al. |
| 6,217,878 B1 | 4/2001 | Menon et al. |
| 6,238,696 B1 | 5/2001 | Wang |
| 6,379,716 B2 | 4/2002 | Santhanam et al. |
| 6,447,815 B1 | 9/2002 | Menon et al. |
| 6,465,442 B2 | 10/2002 | El Khoury |
| 6,482,432 B2 | 11/2002 | Wang |
| 6,511,683 B1 | 1/2003 | Gahler et al. |
| 6,544,530 B1 | 4/2003 | Friedman |
| 6,693,107 B1 | 2/2004 | Simon |
| 6,818,761 B2 | 11/2004 | Giori et al. |
| 6,838,092 B2 | 1/2005 | Mercati |
| 6,881,426 B2 | 4/2005 | Giori et al. |
| 7,135,198 B2 | 11/2006 | Frater-Schroder et al. |
| 7,288,271 B2 | 10/2007 | Graus et al. |
| 7,294,345 B2 | 11/2007 | Haapakumpu et al. |
| 7,303,772 B2 | 12/2007 | Olalde Rangel et al. |
| 7,465,723 B2 | 12/2008 | Schmutz |
| 7,491,414 B2 | 2/2009 | Wang |
| 7,498,360 B2 | 3/2009 | Rask-Andersen et al. |
| 7,597,915 B2 | 10/2009 | Bombardelli |
| 7,682,616 B2 | 3/2010 | Olalde Rangel et al. |
| 7,829,067 B2 | 11/2010 | D'Amelio, Sr. et al. |
| 7,871,647 B1 | 1/2011 | Paradise |
| 7,959,953 B2 | 6/2011 | Zimmerman et al. |
| 7,964,221 B2 | 6/2011 | Pylypchuk |
| 7,964,224 B2 | 6/2011 | Beavers |
| 8,025,909 B2 | 9/2011 | Jarvis et al. |
| 8,062,680 B2 | 11/2011 | Olalde Rangel |
| 8,075,924 B2 | 12/2011 | Loewy et al. |
| 8,075,926 B2 | 12/2011 | Levine et al. |
| 8,101,208 B2 | 1/2012 | Lakkis et al. |
| 8,206,762 B2 | 6/2012 | Freund et al. |
| 8,247,006 B2 | 8/2012 | Golio |
| 8,268,866 B2 | 9/2012 | Guitton et al. |
| 8,273,385 B1 | 9/2012 | Shine |
| 2002/0009508 A1 | 1/2002 | Santhanam et al. |
| 2002/0028258 A1 | 3/2002 | Mitscher et al. |
| 2002/0146473 A1 | 10/2002 | Menon et al. |
| 2003/0104076 A1 | 6/2003 | Berkulin et al. |
| 2003/0152653 A1 | 8/2003 | Gahler et al. |

(Continued)

FOREIGN PATENT DOCUMENTS

| | | | |
|---|---|---|---|
| WO | WO 2008104076 A1 | * | 9/2008 |
| WO | WO 2009023918 A1 | * | 2/2009 |

OTHER PUBLICATIONS

Website document entitled "Ear-Heal" (available at http://www.nativeremedies.com/products/earheal-support-ear-health.html). Downloaded from website Jan. 7, 2014.*
Barnes et al. (2005) J. Pharmacy and Pharmacology 57: 929-954.*
Barrett (2003) Phytomedicine 10: 66-86.*
Stanisavljevic et al. (2009) Chinese J. Chem. Engineering 17(3): 478-483.*
Brinkeborn et al. (1999) Phytomedicine, vol. 6(1), pp. 1-5.*
Website document entitled: "Ear drop" (available at http://en.wikipedia.org/wiki/Ear-drop). Downloaded from website Jun. 26, 2014. Archived to Sep. 13, 2006 @ www.archive.org..*
Website document entitled: "Ear infections (Otitis Media)" (available at http://www.dcnutrition.com/problems/Detail.CFM?RecordNumber-353) Downloaded from website: Jun. 20, 2014. Archived to Jul. 2, 2001 @ www.archive.org.*

*Primary Examiner* — Chris R Tate
*Assistant Examiner* — Russell Fiebig
(74) *Attorney, Agent, or Firm* — Mitchell A. Rossman; Terra Nova Patent Law, PLLC

(57) ABSTRACT

The present invention provides a method of topically treating an otological disorder in a patient in need thereof. The method includes administering topically inside an ear a therapeutically effective amount of composition including an alkyl alcohol; and an *Echinacea* tincture.

11 Claims, No Drawings